(12) United States Patent
Delannay et al.

(10) Patent No.: US 8,013,210 B2
(45) Date of Patent: Sep. 6, 2011

(54) MULTI-GENERATIONAL PHARMACEUTICALLY ACTIVE PROTEIN PRODUCTION IN CORN

(75) Inventors: Xavier Delannay, Defiance, MO (US); Dennis J. Dunphy, Kirkwood, MO (US); Fernando Gaitan-Gaitan, Middleton, WI (US); Thomas P. Jury, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 1354 days.

(21) Appl. No.: 10/832,441

(22) Filed: Apr. 27, 2004

(65) Prior Publication Data

US 2004/0268430 A1 Dec. 30, 2004

Related U.S. Application Data (60) Provisional application No. 60/465,803, filed on Apr. 28, 2003.

(51) Int. Cl.
*A01H 1/02* (2006.01)
*C12N 15/82* (2006.01)
*C12N 15/12* (2006.01)
*C12P 21/00* (2006.01)

(52) U.S. Cl. ........ 800/275; 800/260; 800/274; 800/288; 435/69.4; 435/69.5; 435/69.6

(58) Field of Classification Search .................. 800/260, 800/275, 320.1, 274, 288; 435/69.4, 69.5, 435/69.6

See application file for complete search history.

(56) References Cited

U.S. PATENT DOCUMENTS 5,704,160 A 1/1998 Bergquist et al.
5,706,603 A 1/1998 Bergquist et al.

FOREIGN PATENT DOCUMENTS

EP 0 372 358 6/1990
WO 92/08341 5/1992

OTHER PUBLICATIONS

Zhong et al. 1999. Molecular Breeding 5: 345-356.*
Hood et al. 1997. Molecular Breeding 3: 291-306.*
Pixley et al. 2002. Crop Sci. 42: 1882-1890.*
Austin et al., "An Overview of a Feasibility Study for the Production of Industrial Enzymes in Transgenic Alfalfa", *Ann. N.Y. Acad. Sci.* 721:234-244 (1994).
Bernstein, "Amylases and Carbohydrates in Developing Maize Endosperm", *American Journal of Botany*, 517-516 (1943).
Curtis et al., "Effect of the Pollen Parent on Oil Content of the Corn Kernel", *Agronomy Journal* 48(12):551-555 (1956).
Goddijn and Pen, "Plants as bioreactors", *Trends in Biotechnol.*, 13:379-387 (1995).
Hayes, *Breeding Crop Plants* Second Edition, Fifth Impression, pp. 253-257, McGraw-Hill Book Company, Inc. (1927).
Jones et al., "Hybrid Field Corn", *Connecticut Agricultural Experiment* Bulletin 532 (1949).
Kisselbach, "The Significance of Xenia Effects on the Kernel Weight of Corn", *Research Bulletin* 191:1-30 (1960).
Leng, "Direct Effect of Pollen Parent on Kernel Size in Dent Corn", *Agronomy Journal* 555-558 (1949).
Misevic et al., "Population Cross Diallel among High Oil Populations of Maize", *Crop Sci.* 29:613-617 (1989).
Olson et al., "Nutritional Qualities of Cereal Grains: Genetic and Agronomic Improvement", *Agronomy* 28:199-216 (1987).
Pinter et al., "Effect of Metaxenia on the Grain Weight of the Corn (*Zea mays* L.)", *Maydica XXXII* 81-88 (1987).
Poehlman, *Breeding Field Crops*, Third Edition, Chapter 18, pp. 451-507 (1988).
Ponstein et al., "Production of Enzymes for Industrial Use", *Ann. NY Acad. Sci.* 792:91-98 (1996).
Translation of Ruskova, "Effect of Direction of Crossing on Content of Fats, Proteins and Lysine in Maize Grain", *Genet. Sel.* 7(5):353-360 (1974).
Sprague et al., *Corn and Corn Improvement*, Third Edition, Chapter 16-2.2 (1988).
Abstract of Tikhonov, "Xenia in genetical investigations and in practical breeding", *Genetics* 575:30-41 (1935).
Wilkinson et al., "Genotype, Medium, and Genotype X Medium Effects on the Establishment of Regenerable Maize Callus", *Maydica* XXXIII 89-105 (1987).
Watson, Stanley A. Ed., *Corn: Chemistry and Technology*, Chapter VIII "Corn Wet-Milling Feed Products", 457-459, 1987.

* cited by examiner

*Primary Examiner* — David T Fox
*Assistant Examiner* — Keith O. Robinson
(74) *Attorney, Agent, or Firm* — Chunping Li; Arnold & Porter LLP (57) ABSTRACT

The present invention provides multi-generational production methods for producing pharmaceutically active proteins and other proteins in corn. The present invention also provides methods for breeding corn capable of producing pharmaceutically active proteins or other proteins.

13 Claims, 7 Drawing Sheets

MULTI-GENERATIONAL PHARMACEUTICALLY ACTIVE PROTEIN PRODUCTION IN CORN

CROSS REFERENCE TO RELATED APPLICATION

This application claims benefit under 35 U.S.C. §119(e) of U.S. Provisional Application No. 60/465,803, filed Apr. 28, 2003, in the United States Patent and Trademark Office, the disclosure of which is hereby incorporated by reference in its entirety.

FIELD OF THE INVENTION

The present invention provides multi-generational production methods for producing pharmaceutically active proteins and other proteins in corn. The present invention also provides methods for breeding corn capable of producing pharmaceutically active proteins or other proteins.

BACKGROUND OF THE INVENTION

An ability to produce commercially useful levels of pharmaceutically active proteins in plants in early generations is important to support pre-clinical and clinical trials of such proteins. Traditional commercial manufacture of pharmaceutically active proteins in plants requires transformation of a desired transgenic plant with the nucleic acid molecule of interest and subsequent selection and breeding over multiple generations. Such an approach often fails to deliver commercially useful quantities of the pharmaceutically active protein in early generations such as the $R_0$, $R_1$ and $R_2$ generations. Moreover, many traditional approaches require partial destruction of valuable seed stock to provide protein and to determine either the genotype or phenotype of the seed during the breeding process.

Traditional methods for the manufacture of pharmaceutically active proteins in plants often required transformation, growing the $R_0$ generation with subsequent selfing and selection to generate at least two to three more generations, up to the $R_3$, that could be bulked up for commercial production of the desired pharmaceutically active protein. After the appropriate transgenic events have been selected, large scale production of the active proteins becomes the focus of the process. The use of such corn hybrids for protein production is common. The development of corn hybrids requires the development of inbred lines, the crossing of these lines, and the evaluation of the crosses. A hybrid corn variety includes those varieties that are the cross of two or more such inbred lines, each of which may have one or more desirable characteristics lacked by the other or which complement the other. The new inbreds are crossed with other inbred lines and the hybrids from these crosses are evaluated to determine which have commercial potential. There are several alternatives to produce hybrids from two, three and four inbred lines. They are known as single, triple and double hybrids respectively. The progeny of the first generation produced by such crosses are designated as $F_1$. In the development of hybrids only the $F_1$ hybrid plants are sought, as an $F_1$ hybrid is more vigorous than its inbred parents.

Nonetheless, transgenic plants are potentially one of the most economical systems for large-scale production of recombinant proteins for industrial and pharmaceutical uses (Austin et al., *Ann. NY Acad. Sci.*, 721:235-244 (1994); Krebbers et al., In: P. R. Shewry and S. Gutteridges (eds.), *Plant Protein Engineering*, pp. 315-325, Cambridge University Press, London (1992); Pen et al., In: A. Hiatt (ed.), *Transgenic Plants fundamentals and Applications*, pp. 239-251, Marcel Dekker, New York (1993); Whitelam et al., *Biotechnol. Genet. Eng. Rev.*, 11:1-29 (1993)). Advantages of plant systems often include, the low cost of growing plants on large acreage; the ease in scale-up (increase of planted acreage); the availability of natural protein storage organs; and the established practices for the efficient harvesting, transporting, storing, and processing (Whitelam et al., supra; Goddijn and Pen, *Trends Biotechnol.*, 13:379-387 (1995); Ponstein et al., *Ann. NY Acad. Sci*, 792:92-98 (1996)).

There is a need to provide commercially significant quantities of pharmaceutically active proteins in early plant generations such as $R_0$, $R_1$ and $R_2$. The methods of the present invention provide approaches to deliver commercially significant quantities of pharmaceutically active proteins in such generations. Moreover, the methods of the present invention provide methods that do not require destruction of valuable stock to produce commercially significant quantities of pharmaceutically active proteins.

SUMMARY OF THE INVENTION

The present invention includes and provides a method of producing a pharmaceutically active protein in multiple generations comprising: (a) obtaining a fertile $R_0$ corn plant, wherein the genome of the $R_0$ corn plant comprises a nucleic acid molecule encoding the pharmaceutically active protein; (b) cross-pollinating a first set of hybrid corn plants and a first set of heterotic inbred corn plants with pollen produced by the $R_0$ corn plant; (c) harvesting grain on the first set of hybrid corn plants and harvesting seed on the first set of heterotic corn plants; (d) isolating the pharmaceutically active protein from the grain on the hybrid plant; (e) planting and growing the seed from the heterotic corn to form $F_1$ hybrid plants; (f) cross-pollinating male sterile recipient $F_1$ hybrid plants with the $F_1$ hybrid plants; and (g) isolating the pharmaceutically active protein from at least grain of the male sterile recipient plants.

The present invention also includes and provides a method of producing a pharmaceutically active protein in multiple generations comprising: (a) obtaining a fertile $R_0$ corn plant, wherein the genome of the corn plant comprises a nucleic acid molecule encoding the pharmaceutically active protein; (b) cross-pollinating a first set of hybrid corn plants and a first set of heterotic corn plants with pollen produced by the $R_0$ corn plant; (c) harvesting grain on the hybrid corn plant and harvesting seed on the heterotic corn plant; (d) isolating the pharmaceutically active protein from the grain on the hybrid plant; (e) planting, growing, and pollinating the seed from the heterotic corn to form $F_1$ hybrid plants; and (f) isolating the pharmaceutically active protein from grain of $F_1$ hybrid plants.

The present invention also includes and provides a method of producing a pharmaceutically active protein comprising: (a) obtaining a fertile $R_0$ or $R_1$ corn plant, wherein the genome of the corn plant comprises a nucleic acid molecule encoding the pharmaceutically active protein; (b) cross-pollinating a hybrid corn plant with pollen from the fertile $R_0$ or $R_1$ corn plant, wherein the pharmaceutically active protein is expressed in at least one seed of the hybrid corn plant; (c) harvesting grain of the hybrid plant; and (d) isolating the pharmaceutically active protein from the harvested grain, wherein the average yield of the pharmaceutically active protein is greater than 0.05 mg per gram of dry grain tissue.

The present invention also includes and provides a method of producing a pharmaceutically active protein in corn plants comprising: (a) obtaining a group of fertile corn $R_0$ plants, wherein the plants comprise a nucleic acid molecule encoding the pharmaceutically active protein; (b) pollinating at least two recipient corn plants with pollen from the fertile corn $R_0$ plant, wherein the pharmaceutically active protein is expressed in seeds of the recipient plants; (c) harvesting from grain of recipient corn plants; and (d) isolating the pharmaceutically active protein from the grain of the recipient corn plants, wherein the yield of the pharmaceutically active protein is greater than 0.005 mg per gram of dry grain tissue weight.

The present invention also includes and provides a method of producing a pharmaceutically active protein comprising: (a) obtaining a fertile $R_1$ corn plant, wherein the genome of the $R_1$ corn plant comprises a nucleic acid molecule encoding the pharmaceutically active protein; (b) cross-pollinating a set of heterotic corn plants with pollen produced by the $R_1$ corn plant; (c) planting and growing the seed from the heterotic corn to form $F_1$ hybrid plants; (d) cross-pollinating male sterile recipient plants with the $F_1$ hybrid plants; and (e) isolating the pharmaceutically active protein from at least grain of the male sterile recipient plants.

The present invention also includes and provides a method of simultaneously producing a pharmaceutically active protein and $R_1$ seed comprising: (a) obtaining fertile $R_0$ corn plants, wherein the genome of the $R_0$ corn plants comprises a nucleic acid molecule encoding the pharmaceutically active protein; (b) cross-pollinating a set of hybrid corn plants and a set of recipient corn plants with pollen produced by the $R_0$ corn plant; (c) harvesting grain on the set of hybrid corn plants and harvesting seed on the set of recipient corn plants; and (d) isolating the pharmaceutically active protein from the grain on at least the set of hybrid plants.

The present invention also includes and provides a method of selecting an $R_1$ seed and producing a pharmaceutically active protein comprising: (a) obtaining a fertile $R_0$ corn plant, wherein the genome of the $R_0$ corn plant comprises a nucleic acid molecule encoding the pharmaceutically active protein; (b) cross-pollinating a first set of hybrid corn plants, a first set of heterotic corn plants with pollen produced by the $R_0$ corn plant and a test corn plant with pollen from the fertile $R_0$ corn plant, wherein the pharmaceutically active protein is expressed in at least a seed of the test corn plant; (c) harvesting grain on the hybrid corn plant and harvesting seed on the heterotic corn plant to make $F_1$ seed; (d) isolating the pharmaceutically active protein from the grain on the hybrid plant; (e) planting and growing the seed on the heterotic corn to form $F_1$ hybrid plants; (f) cross-pollinating male sterile recipient plants with the $F_1$ hybrid plants; (g) isolating the pharmaceutically active protein from at least grain of the male sterile recipient plants; and (h) determining the level of the pharmaceutically active protein in the seed of the test corn plant and selecting the $R_1$ seed based on the level of the pharmaceutically active protein in the seed of the test corn plant.

The present invention also includes and provides a non-destructive method of selecting $R_1$ or $F_1$ seed capable of expressing a pharmaceutically active protein comprising: (a) obtaining a fertile $R_0$ corn plant, wherein the plant is transformed with a nucleic acid molecule encoding the pharmaceutically active protein; (b) pollinating a test corn plant with pollen from the fertile $R_0$ corn plant, wherein the pharmaceutically active protein is expressed in at least a seed of the test corn plant; (c) determining a level of the pharmaceutically active protein in the seed of the test corn plant; (d) crossing or selfing the $R_0$ corn plants to form $R_1$ seed or $F_1$ seed; and (e) selecting the $R_1$ seed or $F_1$ seed based on the level of the pharmaceutically active protein in the seed of the test corn.

The present invention also includes and provides a non-destructive method to evaluate the expression of a pharmaceutically active protein in a corn seed comprising: (a) obtaining a fertile $R_0$ corn plant, wherein the plant comprises a nucleic acid molecule encoding the pharmaceutically active protein; (b) pollinating a test corn plant with pollen from the fertile $R_0$ corn plant, wherein the pharmaceutically active protein is expressed in at least a seed of the test corn plant; and (c) determining a level of the pharmaceutically active protein in the seed of the test corn plant.

The present invention also includes and provides a method of producing a pharmaceutically active protein comprising: (a) obtaining a fertile $R_2$ corn plant, wherein the genome of the $R_2$ corn plant comprises a nucleic acid molecule encoding the pharmaceutically active protein; (b) cross-pollinating a set of cytoplasmic male sterile heterotic corn plants with pollen produced by the $R_2$ corn plant; (c) planting and growing the seed on the set of cytoplasmic male sterile heterotic corn to form $F_1$ hybrid plants; (d) cross-pollinating the $F_1$ hybrid plants with male fertile donor corn plants; and (e) isolating the pharmaceutically active protein from at least grain of the male sterile corn plants.

The present invention also includes and provides a method of producing a pharmaceutically active protein comprising: (a) obtaining a fertile $R_3$ corn plant, wherein the genome of the $R_3$ corn plant comprises a nucleic acid molecule encoding the pharmaceutically active protein; (b) cross-pollinating a first set of cytoplasmic male sterile heterotic corn plants with pollen produced by the $R_3$ corn plant; (c) planting and growing the seed on the cytoplasmic male sterile heterotic corn to form $F_1$ hybrid plants; (d) cross-pollinating the $F_1$ hybrid plants with male fertile donor corn plants; and (e) isolating the pharmaceutically active protein from at least grain of the $F_1$ hybrid plants.

The present invention also includes and provides a method of producing a pharmaceutically active protein comprising: (a) obtaining a fertile $R_4$ or later generation corn plant, wherein the genome of the $R_4$ or later generation corn plant comprises a nucleic acid molecule encoding the pharmaceutically active protein; (b) cross-pollinating a first set of cytoplasmic male sterile heterotic corn plants with pollen produced by the $R_4$ or later generation corn plant; (c) planting and growing the seed on the cytoplasmic male sterile heterotic corn to form $F_1$ hybrid plants; (d) cross-pollinating the $F_1$ hybrid plants with male fertile donor corn plants; and (e) isolating the pharmaceutically active protein from at least grain of the $F_1$ hybrid plants.

DETAILED DESCRIPTION OF THE INVENTION

Definitions

As used herein, a "male sterile plant" is any plant that produces, under a particular growing environment, less than 20% of the pollen of a corn plant with a similar genetic background, but lacking the male sterility trait.

As used herein, an "$R_0$ plant" is a plant that is regenerated from a transformation event. For example, without limitation, $R_0$ plants can be utilized as male fertile pollinator in combination with any aspect of the present invention. Such uses include, again without limitation, grain production or breeding.

As used herein, an "$R_1$ seed" is the seed generated from selfing or backcrossing an $R_0$ plant. An $R_1$ plant is a plant grown from an $R_1$ seed.

As used herein, an "$R_2$ seed" is a seed generated from selfing or backcrossing an $R_1$ plant. An $R_2$ plant is a plant generated from an $R_2$ seed.

As used herein, an "$R_3$ seed" is a seed generated from selfing or backcrossing an $R_2$ plant. An $R_3$ plant is a plant generated from an $R_3$ seed.

As used herein, an "$R_4$ seed" is a seed generated from selfing or backcrossing an $R_3$ plant. An $R_4$ plant is a plant generated from an $R_4$ seed.

As used herein, a "recipient seed or plant" is a seed or plant with a seed that is pollinated by the pollen of a plant. A recipient seed or plant with a seed can be self-pollinated (selfed).

As used herein, two corn plants are "heterotic" to each other when a progeny generated from a cross between such plants exhibits a hybrid vigor that is associated with outbreeding, hybridity or levels of heterozygosity.

As used herein, "similar genetic background" is a background where the plants being compared share 50% or greater of their nuclear genetic material. In a more preferred aspect, a "similar genetic background" is a background where the organisms being compared share 75% or greater, even more preferably 90% or greater of their nuclear genetic material. In another even more preferable aspect, a "similar genetic background" is a background where the plants are isogenic except for any genetic material originally introduced using plant transformation techniques.

As used herein, "grain" is corn seed that is harvested for uses other than re-planting.

As used herein, "harvesting" means any applicable methodology to obtain a plant or part thereof such as a seed or grain. Such harvesting can be of one or more seeds or grains.

As used herein, the term "polypeptide" encompasses proteins and peptides as well as polypeptides within its scope, and refers to both naturally-occurring chemical entities and structurally similar bioactive equivalents thereof.

As used herein, the term "pharmaceutically active protein" is any substantially purified translation product of a polynucleotide regardless of size, and whether glycosylated or not, capable of providing a therapeutic effect in a mammal.

As used herein, the term "antibody" refers to a polypeptide comprising a framework region from an immunoglobulin gene or fragments thereof that specifically binds and recognizes an antigen. Antibodies may be monoclonal or polyclonal. Antibodies include recombinant proteins (such as chimeric or humanized antibodies and antibody fusions) comprising the binding domains, as well as fragments. Antibody fragments are defined as a portion of an intact antibody comprising the antigen binding site or variable region of the intact antibody, wherein the portion is free of the constant heavy chain domains (i.e. $CH_2$, $CH_3$ and $CH_4$, depending on antibody isotype) of the Fc region of the intact antibody. Examples of antibody fragments include, without limitation, (i) the Fab fragment consisting of VL, VH, CL and $CH_1$ domains; (ii) the Fd fragment consisting of the VH and $CH_1$ domains; (iii) the Fv fragment consisting of the VL and VH domains of a single antibody; (iv) the dAb fragment (Ward et al., *Nature,* 341:544-546 (1989)) which consists of a VH domain; (v) isolated CDR regions; (vi) $F(ab')_2$ fragments, a bivalent fragment including two linked Fab fragments; (vii) single chain Fv molecules (scFv), wherein a VH domain and a VL domain are linked by a peptide linker which allows the two domains to associate to form an antigen binding site (Bird et al., *Science,* 242:423-426 (1988); Huston et al., *Proc. Natl. Acad. Sci. USA,* 85:5879-5883 (1988)); (viii) bispecific single chain Fv dimers (PCT/US92/09965); and (ix) "diabodies," multivalent or multispecific fragments constructed by gene fusion (WO 94/13804; Holliger et al., *Proc. Natl. Acad. Sci. USA,* 90:6444-6448 (1993)).

As used herein, "chimeric antibody" is an antibody molecule in which (a) the constant region, or a portion thereof, is altered, replaced or exchanged so that the antigen binding site (variable region) is linked to a constant region of a different or altered class, subclass and/or species. See Queen et al., *Proc. Natl. Acad. Sci. USA* 86:10029-10033 (1989); WO 90/07861; Morrison et al., *Proc. Natl. Acad. Sci. USA,* 81:6581 (1984); Fell et al., U.S. Pat. No. 5,202,238.

As used herein, a "humanized antibody" is an antibody molecule in which the constant regions are derived from human, and the variable regions are modified to be more human-like. This can be carried out by engineering the discrete segments of the variable region responsible for antigen binding (called the complementarity determining regions, CDR) into human framework regions. See Queen et al., *Proc. Natl. Acad. Sci. USA* 86:10029-10033 (1989) and WO 90/07861.

As used herein, a "human antibody" is an antibody molecule which is entirely derived from human antibody sequences. It may be identical to an antibody produced in a human antibody-producing cell, or engineered from different human-derived or human-identical fragments.

As used herein, an "antibody fusion" is an antibody molecule or portion thereof fused to an entirely different molecule that adds new properties to the antibody, e.g., an enzyme, toxin, hormone, growth factor, drug, heterologous antibody or fragment, etc.

As used herein, a "plant transformation technique" is any technique that provides for the incorporation of DNA in a genome of a plant by a technique where the DNA is manipulated outside a plant cell in a step prior to its introduction into the plant cell.

DETAILED DESCRIPTION

The present invention provides methods and approaches that allow for the delivery of commercially useful quantities of pharmaceutically active proteins in multiple generations and is particularly advantageous in that it can provide commercially useful quantities of pharmaceutically active proteins in early generations such as $R_0$, $R_1$, and $R_2$. Such delivery does not require the destruction of valuable $R_0$ seed, $R_1$ seed, or $R_2$ seed.

For example, the present invention provides a method of producing a pharmaceutically active protein in multiple generations comprising: (a) obtaining a fertile $R_0$ corn plant, wherein the genome of the $R_0$ corn plant comprises a nucleic acid molecule encoding the pharmaceutically active protein; (b) cross-pollinating a first set of hybrid corn plants and a first set of heterotic corn plants with pollen produced by the $R_0$ corn plant; (c) harvesting grain on the first set of hybrid corn plants and harvesting seed on the first set of heterotic corn plants; (d) isolating the pharmaceutically active protein from the grain on the hybrid plant; (e) planting and growing the seed from the heterotic corn to form $F_1$ hybrid plants; (f) cross-pollinating male sterile recipient plants with the $F_1$ hybrid plants; and (g) isolating the pharmaceutically active protein from at least grain of the male sterile recipient plants.

While it is understood that the methods or approaches of the present invention can be used to produce any protein or polypeptide, in a preferred aspect that protein or polypeptide is a pharmaceutically active protein. Moreover, while the methods of the present invention are described with respect to pharmaceutically active proteins, it is understood that non-pharmaceutically active proteins may be substituted and produced by any of the disclosed methods.

Pharmaceutically active proteins include, without limitation, those polypeptides that can compensate for a defective or deficient species in a mammal, or those that act through toxic effects to limit or remove harmful cells from the body. In addition, the polypeptides or proteins used in the present invention can include, without limitation, vaccines, antibodies or fragments thereof, antigens, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, human pancreas hormone releasing factor, human tissue plasminogen activator, human tumor necrosis factor, carbohydrates, nucleotides, and the like, and structurally similar bioactive equivalents thereof. By "structurally similar bioactive equivalent" is meant a polypeptide with an amino acid sequence which, although not identical to that of the naturally occurring polypeptide or protein, is sufficiently similar in structure to produce substantially equivalent therapeutic effects on the subject to that produced by the natural polypeptide or protein itself.

In a preferred aspect, the pharmaceutically active protein is an antibody, more preferably a humanized antibody, chimeric antibody, or a human antibody.

A fertile $R_0$ corn plant comprising one or more copies of a nucleic acid molecule that encodes a pharmaceutically active protein can be obtained by any plant transformation technique. Multiple techniques are known for the transformation of corn (see, e.g., U.S. Pat. Nos. 6,476,295 and 6,469,234). Moreover, any suitable corn plant may be transformed. Illustrative inbreds that can be transformed are A634 and LH59. For example, a generally applicable method of plant transformation is microprojectile-mediated transformation where DNA is carried on the surface of microprojectiles measuring about 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol*, 5:27 (1987); Sanford, *Trends Biotech,* 6:299 (1988), Klein et al., *Bio/Technology,* 6:559-563 (1988), Sanford, *Physiol. Plant,* 7:206 (1990), Klein et al., *Biotechnology,* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology,* 9:996 (1991). Alternatively, liposome or spheroplast fusion have been used to introduce expression vectors into plants. Deshayes et al., *EMBO J.,* 4:2731 (1985), Christou et al., *Proc. Natl. Acad. Sci. USA,* 84:3962 (1987). Direct uptake of DNA into protoplasts using $CaCl_2$ precipitation, polyvinyl alcohol or poly-L-ornithine have also been reported. Hain et al., *Mol. Gen. Genet.,* 199:161 (1985) and Draper et al., *Plant Cell Physiol.,* 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., *Plant Cell,* 4:1495-1505 (1992); and Spencer et al., *Plant Mol. Biol.,* 24:51-61 (1994). *Agrobacterium* can also be used to deliver DNA.

The regeneration, development and cultivation of corn from single plant protoplast transformants or from various transformed explants is well known in the art (Weissbach and Weissbach, in: *Methods for Plant Molecular Biology*, Academic Press, San Diego, Calif. (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

Exogenous genetic material may be transferred into a host cell by the use of a DNA vector or construct designed for such a purpose. Design of such a vector is generally within the skill of the art (see, *Plant Molecular Biology: A Laboratory Manual*, Clark (ed.), Springer, New York (1997)).

A construct or vector may include a plant promoter to express the pharmaceutically active protein or polypeptide of choice. In a preferred embodiment, any nucleic acid molecules encoding a pharmaceutically active protein or other polypeptide can be operably linked to a promoter region which functions in a plant seed cell to cause the production of an mRNA molecule.

Promoters utilized to drive gene expression in transgenic plants can be derived from many sources so long as the chosen promoter(s) have sufficient transcriptional activity to accomplish the invention by expressing translatable mRNA. For example, promoters for expression in a wide array of plant organs include those directing the 19S and 35S transcripts in cauliflower mosaic virus (Odell et al., *Nature,* 313:810-812 (1985); Hull et al., *Virology,* 86:482-493 (1987)), small subunit of ribulose 1,5-bisphosphate carboxylase (Morelli et al., *Nature,* 315:200-204 (1985); Broglie et al., *Science,* 224:838-843 (1984); Hererra-Estrella et al., *Nature,* 310:115-120 (1984); Coruzzi et al., *EMBO J.,* 3:1671-1679 (1984); Faciotti et al., *Bio/Technology,* 3:241 (1985)) and chlorophyll a/b binding protein (Lamppa et al., *Nature,* 316:750-752 (1986)).

Preferred promoters are those that allow expression specifically in seeds. Examples of seed-specific promoters include, but are not limited to, the promoters of seed storage proteins. The expression of seed storage proteins is regulated in the plant, being expressed almost exclusively in seeds in a highly organ-specific and stage-specific manner (Higgins et al., *Ann. Rev. Plant Physiol.,* 35:191-221 (1984); Goldberg et al., *Cell*, 56:149-160 (1989); Thompson et al., *BioEssays*, 10:108-113 (1989)). Moreover, different seed storage proteins may be expressed at different stages of seed development. There are currently numerous examples for seed-specific expression of seed storage protein genes in transgenic plants. These include genes from monocotyledonous plants such as for barley β-hordein (Marris et al., *Plant Mol. Biol.*, 10:359-366 (1988)) and wheat glutenin (Colot et al., *EMBO J.*, 6:3559-3564 (1987)). Moreover, promoters of seed-specific genes, operably linked to heterologous coding sequences in chimeric gene constructs, also maintain their temporal and spatial expression pattern in transgenic plants (Goldberg et al., *Cell*, 56:149-160 (1989); De Clercq et al., *Plant Physiol.*, 94:970-979 (1990); Riggs et al. *Plant Sci.*, 63:47-57 (1989); Colot et al. *EMBO J.*, 6:3559-3564 (1987)).

Of particular use in the expression of the pharmaceutically active protein encoding sequences of the invention will be promoters from several extensively characterized corn, rice and wheat seed storage protein genes such as endosperm-specific promoters from the 10 kD zein gene (Kirihara et al., *Gene*, 71:359-370 (1988)), the 15 kD zein gene (Hoffman et al. *EMBO J.*, 6:3213-3221 (1987); Schernthaner et al. *EMBO J.*, 7:1249-1253 (1988); Williamson et al., *Plant Physiol.*, 88:1002-1007 (1988)), the 27 kD zein gene (Prat et al. *Gene*, 52:51-49 (1987); Gallardo et al., *Plant Sci.*, 54:211-281 (1988)), the 19 kD zein gene (Marks et al., *J. Biol. Chem.*, 260:16451-16459 (1985)), the rice glutellin gene (Russell and Fromm, *Transgenic Res.* 6:157-68 (1997); Okita et al., *J Biol Chem*, 264:12573-81 (1989)), and the wheat high molecular weight glutenin gene (Lamacchia et al., *J. Exp. Bot.*, 52:243-50 (2001)). The relative transcriptional activities of some of these promoters in corn have been reported (Kodrzyck et al. *Plant Cell*, 1:105-114 (1989)) providing a basis for choosing a promoter for use in chimeric gene constructs for corn. Moreover, promoters that drive the expression of genes encoding enzymes involved in starch biosynthesis may be used in the practice of this invention. These include, but are not limited to, the 5' regulatory sequences of the sucrose synthase (Yang and Russell, *Proc. Natl. Acad. Sci. USA*, 87:4144-4148 (1990)), the waxy or granule-bound starch synthase I (Unger et al., *Plant Physiol.*, 96:124 (1991)) genes, the sh2 (Bhave et al., *Plant Cell*, 2:581-588 (1990)) and bt2 (Bae et al., *Maydica*, 35:317-322 (1990)) genes whose products constitute the enzyme ADP-glucose pyrophosphorylase. A particularly preferred promoter for corn endosperm expression is the promoter for the glutelin gene from rice (WO 98/10062; Zheng et al., *Mol. Cell Biol.*, 13:5829-5842 (1993)).

Expression from any of these promoters could be increased by the use of enhancer sequences, including those found in intron sequences (see, for example, Callis et al., *Genes Dev.*, 1:1183-1200 (1987); Maas et al., *Plant Mol. Biol.*, 16:199-207 (1991); Luehrsen and Walbot, *Mol. Gen. Genet.*, 225:81-93 (1991); Oard et al., *Plant Cell Rep.*, 8:156-160 (1989); Brown et al., U.S. Pat. No. 5,859,347).

A construct or vector may include a 3' non-coding region capable of providing a polyadenylation signal to express the pharmaceutically active protein or polypeptide of choice. Any 3' non-coding region capable of providing a polyadenylation signal and other regulatory sequences that may be required for proper expression can be used to accomplish the invention. This would include the 3' end from any storage protein such as the 3' end of the 10 kD, 15 kD, 27 kD and alpha zein genes, the 3' end of the bean phaseolin gene, the 3' end of the soybean β-conglycinin gene, the 3' end from viral genes such as the 3' end of the 35S or the 19S cauliflower mosaic virus transcripts, the 3' end from the opine synthesis genes, the 3' ends of genes encoding ribulose 1,5-bisphosphate carboxylase or chlorophyll a/b binding protein, or 3' end sequences from any gene such that the sequence employed provides the necessary regulatory information within its nucleic acid sequence to result in the proper expression of the promoter/coding region combination to which it is operably linked. There are multiple examples in the art that teach the usefulness of different 3' non-coding regions (for example, see Ingelbrecht et al., *Plant Cell*, 1:671-680 (1989)).

While we do not wish to be bound by any theory or mechanism advanced to explain the functioning of any aspect of the invention, pollen has an immediate effect on protein expression on the seed. Pollinated seeds will express proteins that are encoded within the genome of the donor pollen when the nucleic acid molecules encoding the proteins are operatively linked to promoters that are capable of expressing the protein in a seed tissue.

In cereal grains such as corn (*Zea mays* L. or maize), the kernel is the product of double fertilization (Kiesselbach, *The Structure and Reproduction of Corn*, University of Nebraska Press (1980)). The pollen grain contains two sperm nuclei. At the time of fertilization, one of the sperm nuclei fuses with the nucleus of the ovule to form the embryo of the seed, and one fuses with two female nuclei to form the endosperm of the seed. The endosperm receives two thirds of its genetic material from the female plant and one third from the pollen. The immediate effect of pollen on the developing seed is often termed xenia. The number of copies of a particular gene present in a cell, such as an endosperm cell, is known as the gene dose. Production methods of the present invention take advantage of the fact that proteins encoded by the genome of pollen can be expressed in the recipient seed.

The present invention provides for the cross-pollination of a hybrid corn plant with pollen produced by one or more $R_0$ plants comprising a nucleic acid encoding a desired pharmaceutically active protein. Cross-pollination of a hybrid corn plant with pollen produced by one or more $R_0$ plants can be cross-pollination of any hybrid corn plant. An illustrative hybrid is LH198xLH172. In a preferred aspect, the hybrid corn is high yielding. In another aspect, the hybrid corn is high yielding and cytoplasmic male sterile or male sterile by other means such as mechanical means. Cytoplasmic male sterile corn hybrids may be male sterile corn hybrids but in a preferred aspect, the male sterile hybrid is selected from the group consisting of cms-T, cms-C, and cms-S.

In a preferred aspect, a male sterile plant produces less than 30% or 20% of the quantity of pollen produced by a co-planted male fertile plant measured at a time of female fertility. In a more preferred aspect, a male sterile plant produces less than 10%, more preferably less than 5%, of the quantity of pollen produced by a co-planted male fertile plant measured at a time of female fertility. In this aspect, % shedding of pollen is measured and averaged across the population of plants being utilized in a method of the present invention.

A high-yielding corn hybrid can be any hybrid that results from a breeding program to produce commercially useful hybrids. A high-yielding corn hybrid can be selected to suit the conditions, region or climate. Examples of such high-yielding hybrids are those commercially sold by seed companies to farmers for use under the desired region, climate, or conditions.

While it is preferred that a hybrid is utilized as the recipient plant for $R_0$ pollen, when protein production is desired, other corn plants can be utilized such as inbreds, partial inbreds, blends, populations, etc.

In methods of the present invention, it is not necessary to screen or select for expression level of a pharmaceutically active protein in an $R_0$ plant or seed or group of plants or seeds prior to cross-pollination of a hybrid plant with pollen produced by one or more $R_0$ plants or group of plants. In a preferred aspect, $R_0$ plants or seeds are not pre-screened or selected for expression level of a pharmaceutically active protein or population. $R_0$ plants or seeds can, nonetheless, be pre-screened or pre-selected for expression level of a pharmaceutically active protein in a $R_0$ plant, if so desired. A determination of the level of expression or the copy number of the nucleic acid molecule encoding the pharmaceutically active protein can also be made in the $R_0$ or subsequent generation. Methods to determine the copy number, genotype or expression level of a nucleic acid molecule or protein are known in the art. Illustrative methods to determine copy number include the use of TaqMan™ (Applied Biosystems, Foster City, Calif.) and Invader™ (Third Wave Technologies, Madison, Wis.). Illustrative methods to detect protein expression include antibody based methodologies such as ELISA (*The Maize Handbook*, Freeling et al. (eds.), Springer-Verlag, New York (1994); *Genome Analysis: A Laboratory Manual*, Vol. 2 ("Detecting Genes"), Birren et al. (eds.), Cold Spring Harbor Laboratory Press (1998); *Antibodies: A Laboratory Manual*, Harlow et al. (eds.), Cold Spring Harbor Laboratory Press (1988); and WO 98/10062). Additional illustrative methods are set forth in Example 3. In an aspect of the present invention, any of the plants or hybrids or seeds thereof can be evaluated for protein yield.

In an aspect of the present invention, a group or set of $R_0$ corn plants can be used to pollinate one or more recipient corn plants for protein production, breeding, or both. Such a group or set of $R_0$ plants can be the result of a single transformation experiment or the result of multiple transformation experiments. In one aspect, the group or set of $R_0$ plants transformed with a nucleic acid molecule encoding a pharmaceutically active protein used to cross-pollinate one or more recipient plants is greater than or equal to 2, 5, 10, 20, 25, 30, 40, 50, 60, 70, 80, 90, 100, 250, 500, 750, 1,000, 1,250, 1,500 or 2,000 $R_0$ plants. Moreover, in this aspect the number of recipient plants is at least or equal to 2, 5, 10, 20, 25, 30, 40, 50, 60, 70, 80, 90, 100, 250, 500, 750, 1,000, 1,250, 1,500 or 2,000 recipient plants.

Grain or seeds can be harvested from any recipient plant by any method that removes seeds from the recipient plants. Methods to remove seeds from corn plants are known in the art. Such methods include manual or mechanical methods.

A corn seed may be planted in soil or a non-soil environment capable of supporting plant growth. Corn seed may be planted in any configuration that allows pollination.

A pharmaceutically active protein may be isolated from grain using any appropriate method of protein purification. Illustrative methods are set forth in WO 98/10062 and in the Examples. It is preferred that the yield of pharmaceutically active protein is greater than 0.001 mg per gram of dry grain tissue in recipient plants pollinated by $R_0$ plants for protein production. In more preferred aspects, the yield of pharmaceutically active protein is greater than 0.01 mg, 0.05 mg, 0.1 mg, 0.3 mg, 0.5 mg, 0.7 mg or 0.9 mg per gram of dry grain tissue in recipient plants pollinated by $R_0$ plants for protein production. As used herein unless otherwise specified, the quantity of pharmaceutically active protein per gram of dry tissue is measured when the grain is dried to a moisture level of between 11 and 15% water and the quantity of the pharmaceutically active protein is measure by a quantitative ELISA assay calibrated with know standards of an appropriate protein prior to use. The seed protein preparation is prepared as Example 3.

Where $R_0$ plants are used to pollinate a recipient plant for protein production in a preferred aspect each $R_0$ plant is used to provide pollen to greater than 2, 3, 4, 5, 6, 7, 8, 9 or 10 recipient plants. In such an aspect, it is preferred that greater than 25, 50, 75, 100, 125, 150, 175, 200, 250 or 300 $R_0$ plants are used such that greater than 50, 100, 200, 300, 400 or 500 mg of a pharmaceutically active protein is produced.

In one aspect, fertile $R_0$ plants cross-pollinate a group or set of heterotic corn plants. In another aspect, which can be combined with cross-pollination of heterotic corn plants, the fertile $R_0$ plants are self-pollinated, backcrossed or both. An illustrative cross to a heterotic corn plant is set forth in Example 2. In a preferred aspect, the heterotic plant is an inbred. An example, without limitation, of a heterotic pair of inbreds is A634 and 90DJD28.

Figure 1:
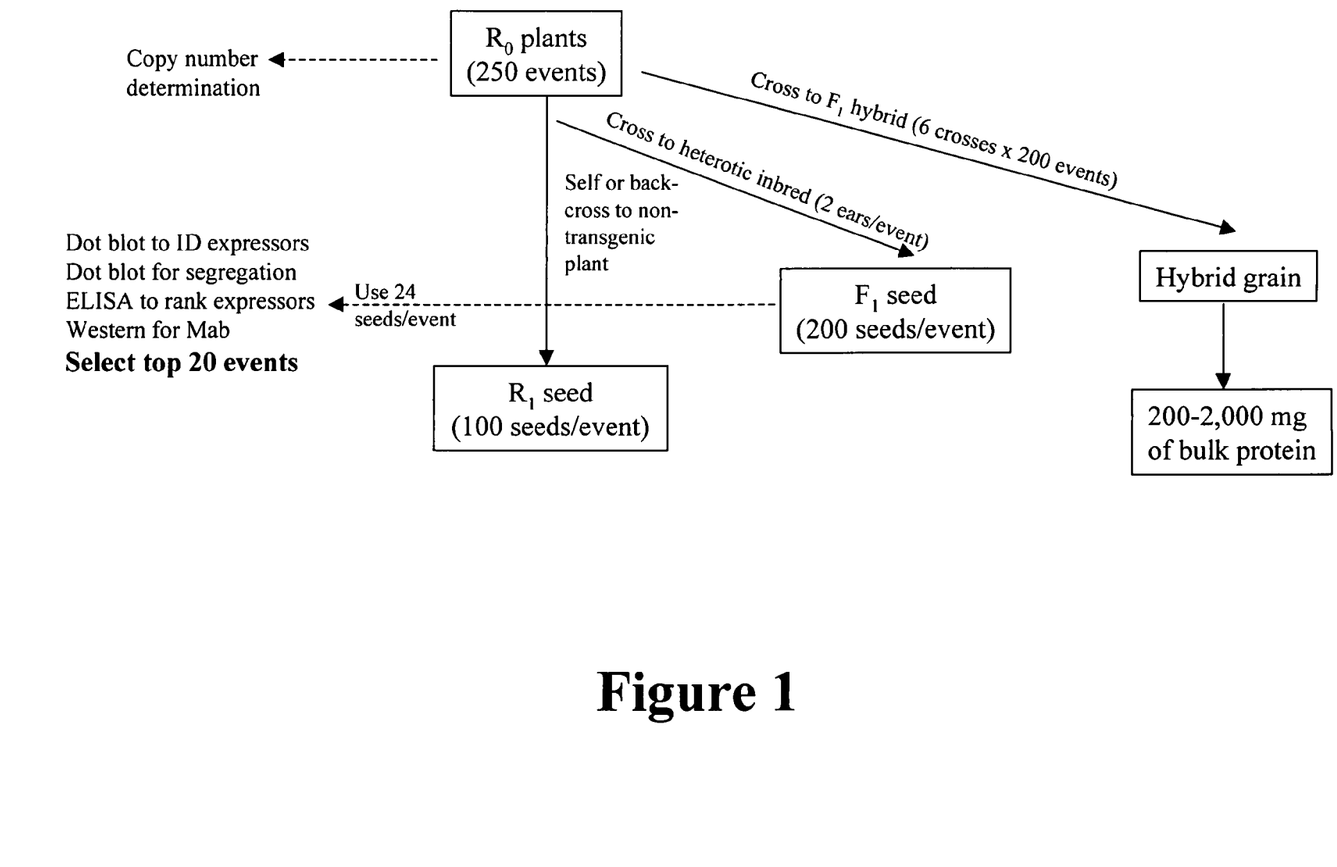
FIG. 1 sets forth an illustrative schematic of a $R_0$ production and breeding approach.

In a preferred aspect, a single set or group of fertile $R_0$ corn plants having a genome comprising a nucleic acid molecule encoding a pharmaceutically active protein can be used to cross-pollinate a recipient plant to generate seed rather than grain, to cross-pollinate heterotic corn plants to form seed and to self-pollinate or be used to backcross to a non-transformed inbred parent. Such an approach is illustrated in FIG. 1. In the preferred aspect where hybrids and heterotic corn plants are pollinated by $R_0$ corn plants and $R_0$ corn plants are selfed or backcrossed it is preferred that the group or set of $R_0$ corn plants is greater than 2, 5, 10, 20, 25, 30, 40, 50, 60, 70, 80, 90, 100, 250, 500, 750, 1,000, 1,250, 1,500 or 2,000 plants. It is further preferred that at least 50%, 60%, 70%, 80%, 90%, 95%, 99% or 100% of the $R_0$ corn plant set or group are independently derived transformants.

Heterotic seed pollinated by $R_0$ corn plants can be planted and grown to produce $F_1$ hybrids $(-/R_0)$. Pharmaceutically active proteins can be isolated from selfed $F_1$ corn hybrids $(-/R_0)$. Alternatively or in combination with isolating pharmaceutically active proteins from the $F_1$ corn hybrids $(-/R_0)$, the $F_1$ corn hybrids $(-/R_0)$ can be used to pollinate a recipient plant. In a preferred aspect, the recipient plant is a non-transgenic cytoplasmic male sterile corn hybrid, preferably a high-yielding hybrid. Illustrative non-transgenic cytoplasmic male sterile hybrids include 90DJD28CMS/A634.

In a preferred aspect, each $R_0$ plant can be used to pollinate two or more heterotic ears or plants. In this aspect, it is preferred that each $R_0$ plant is used to generate more than 25, 50, 75, 100, 150, 200, 250 or 500 $F_1$ hybrid seeds. In a preferred protein production aspect, a set or group of transgenic $F_1$ hybrids $(-/R_0)$ acts to pollinate sufficient non-transgenic or transgenic recipient plants to provide greater than 5,000, 10,000, 12,000, 15,000, 17,000, 19,000 or 21,000 seeds.

In a protein production aspect where transgenic $F_1$ hybrids $(-/R_0)$ are self-pollinated or pollinated, or used to pollinate, sufficient recipient plants are preferred that can provide greater than 2, 3, 4, 5, 6, 7, 8, 9, 10, 15, 20, 25, 50 or 100 grams of pharmaceutically active protein.

$R_0$ plants can be selfed or backcrossed to provide $R_1$ seeds. $R_1$ plants and seeds can be pre-screened or pre-selected for copy number or expression level of a pharmaceutically active protein.

In an aspect of the present invention, a group or set of $R_1$ corn plants can be used to pollinate one or more recipient corn plants for protein production, breeding, or both. Such a group or set of $R_1$ plants can be the result of a single transformation experiment or the result of multiple transformation experiments. In one aspect, the group or set of $R_1$ plants transformed with a nucleic acid molecule encoding a pharmaceutically active protein used to cross-pollinate one or more recipient plants is greater than or equal to 2, 5, 10, 20, 25, 30, 40, 50, 60, 70, 80, 90, 100, 250, 500, 750, 1,000, 1,250, 1,500 or 2,000 $R_1$ plants. Moreover, in this aspect the number of recipient plants is at least or equal to 2, 5, 10, 20, 25, 30, 40, 50, 60, 70, 80, 90, 100, 250, 500, 750, 1,000, 1,250, 1,500 or 2,000 recipient plants.

It is preferred that the yield of pharmaceutically active protein is greater than 0.001 mg per gram of dry grain tissue in recipient plants pollinated by $R_1$ plants for protein production. In more preferred aspects, the yield of pharmaceutically active protein is greater than 0.01 mg, 0.05 mg, 0.1 mg, 0.3 mg, 0.5 mg, 0.7 mg or 0.9 mg per gram of dry grain tissue in recipient plants pollinated by $R_1$ plants for protein production.

The present invention provides for the cross-pollination of a hybrid corn plant with pollen produced by one or more $R_1$ plants transformed with a nucleic acid encoding a desired pharmaceutically active protein. Cross-pollination of a hybrid corn plant with pollen produced by one or more $R_1$ plants can be cross-pollination of any hybrid corn plant.

In one aspect, fertile $R_1$ plants cross-pollinate a group or set of heterotic corn plants. In another aspect, which can be combined with cross-pollination of heterotic corn plants the fertile $R_1$ plants are self-pollinated, backcrossed or both (see FIG. 2). An illustrative cross to a heterotic corn plant is set forth in Example 4. In a preferred aspect, the heterotic plant is an inbred and is cytoplasmically male sterile and such sterility is not restored by the cross.

Figure 2:
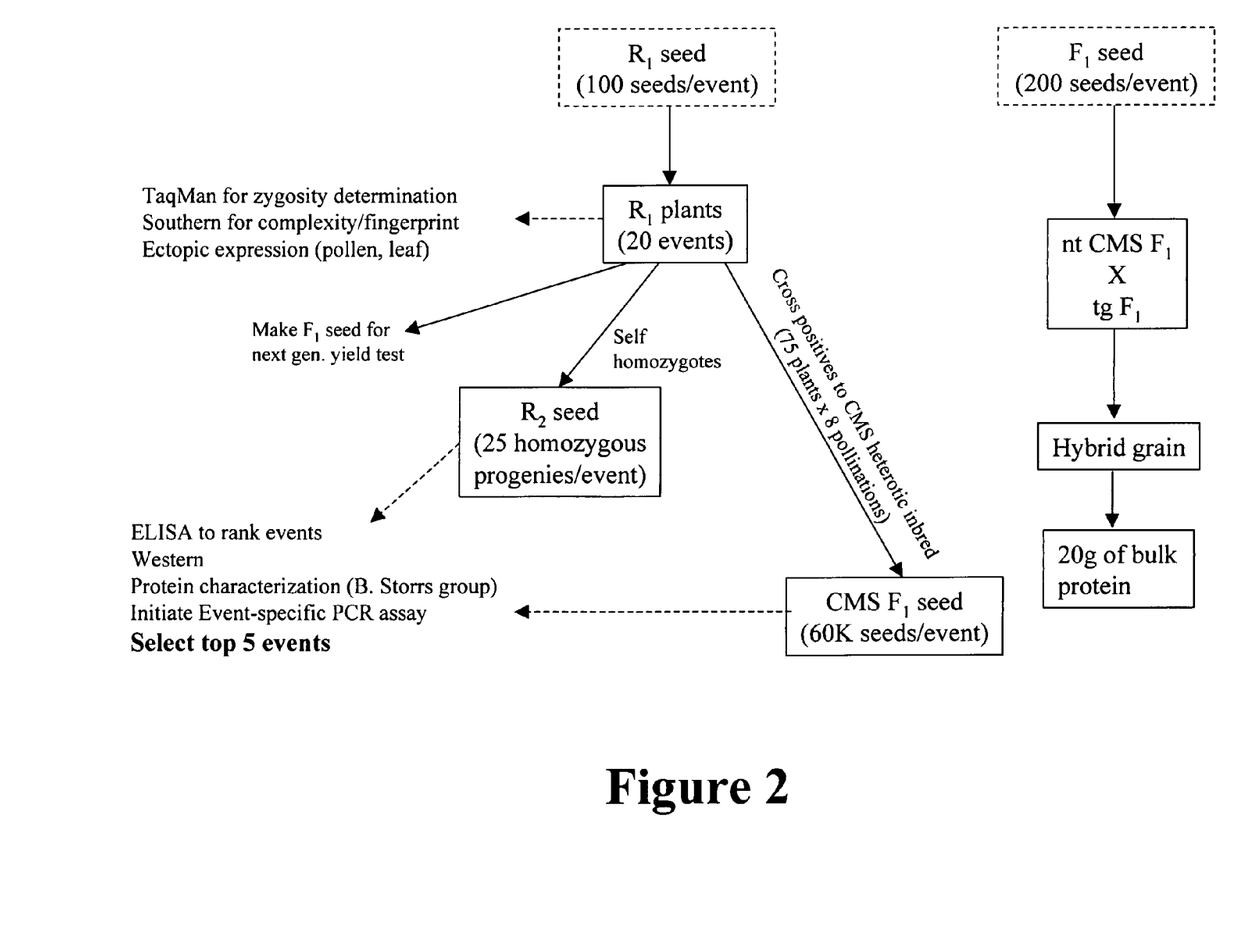
FIG. 2 sets forth an illustrative schematic of a $R_1$ production and breeding approach.

In a preferred aspect, a single set or group of fertile $R_1$ corn plants having a genome comprising a nucleic acid molecule encoding a pharmaceutically active protein can be used to cross-pollinate heterotic corn plants to form seed and to self-pollinate or be used to backcross to a non-transformed inbred parent. Such an approach is illustrated in FIG. 2.

Heterotic plants pollinated by $R_1$ corn plants can be planted and grown to produce $F_1$ hybrids ($-/R_1$). Pharmaceutically active proteins can be isolated from selfed $F_1$ corn hybrids ($-/R_1$). Alternatively or in combination with isolating pharmaceutically active proteins from the $F_1$ corn hybrids, the $F_1$ corn hybrids ($-/R_1$) can be used to pollinate a recipient plant. In a preferred aspect, the recipient plant is a non-transgenic cytoplasmic male sterile corn hybrid, preferably a high-yielding hybrid.

In a preferred aspect, each $R_1$ plant can be used to pollinate two or more heterotic ears or plants. In this aspect, it is preferred that each $R_1$ plant is used to generate more than 200, 400, 600, 800, 1,000, 1,200, 1,400 or 1,600 $F_1$ hybrid seeds ($-/R_1$). In a preferred protein production aspect, a set or group of transgenic $F_1$ hybrids ($-/R_1$) acts to pollinate sufficient non-transgenic or transgenic recipient plants to provide greater than 20,000, 30,000, 40,000, 50,000, 60,000, 70,000, 80,000, 100,000, 150,000 or 200,000 seeds.

In a protein production aspect where transgenic $F_1$ hybrids ($-/R_1$) are self-pollinated or used to pollinate, sufficient recipient plants are preferred that can provide greater than 20, 40, 60, 80, 100, 150, or 200 grams of pharmaceutically active protein.

In a preferred protein production aspect using $R_1$ plants, greater than 25, 50, 75, or 100 $R_1$ plants are used to pollinate greater than 10, 20, 30, 40, 50, 60, 70, 80, 90, or 100 recipient plants.

$R_1$ plants can be selfed or backcrossed to provide $R_2$ seed. $R_2$ plants and $R_2$ seeds can be pre-screened or pre-selected for copy number or expression level of a pharmaceutically active protein.

In an aspect of the present invention, a group or set of $R_2$ corn plants can be used to pollinate one or more recipient corn plants for protein production, breeding, or both. Such a group or set of $R_2$ plants can be the result of a single transformation experiment or the result of multiple transformation experiments. In one aspect, the group or set of $R_2$ plants transformed with a nucleic acid molecule encoding a pharmaceutically active protein used to cross-pollinate one or more recipient plants is greater than or equal to 2, 5, 10, 20, 25, 30, 40, 50, 60, 70, 80, 90, 100, 250, 500, 750, 1,000, 1,250, 1,500 or 2,000 $R_2$ plants. Moreover, in this aspect the number of recipient plants is at least or equal to 2, 5, 10, 20, 25, 30, 40, 50, 60, 70, 80, 90, 100, 250, 500, 750, 1,000, 1,250, 1,500 or 2,000 recipient plants.

Figure 3:
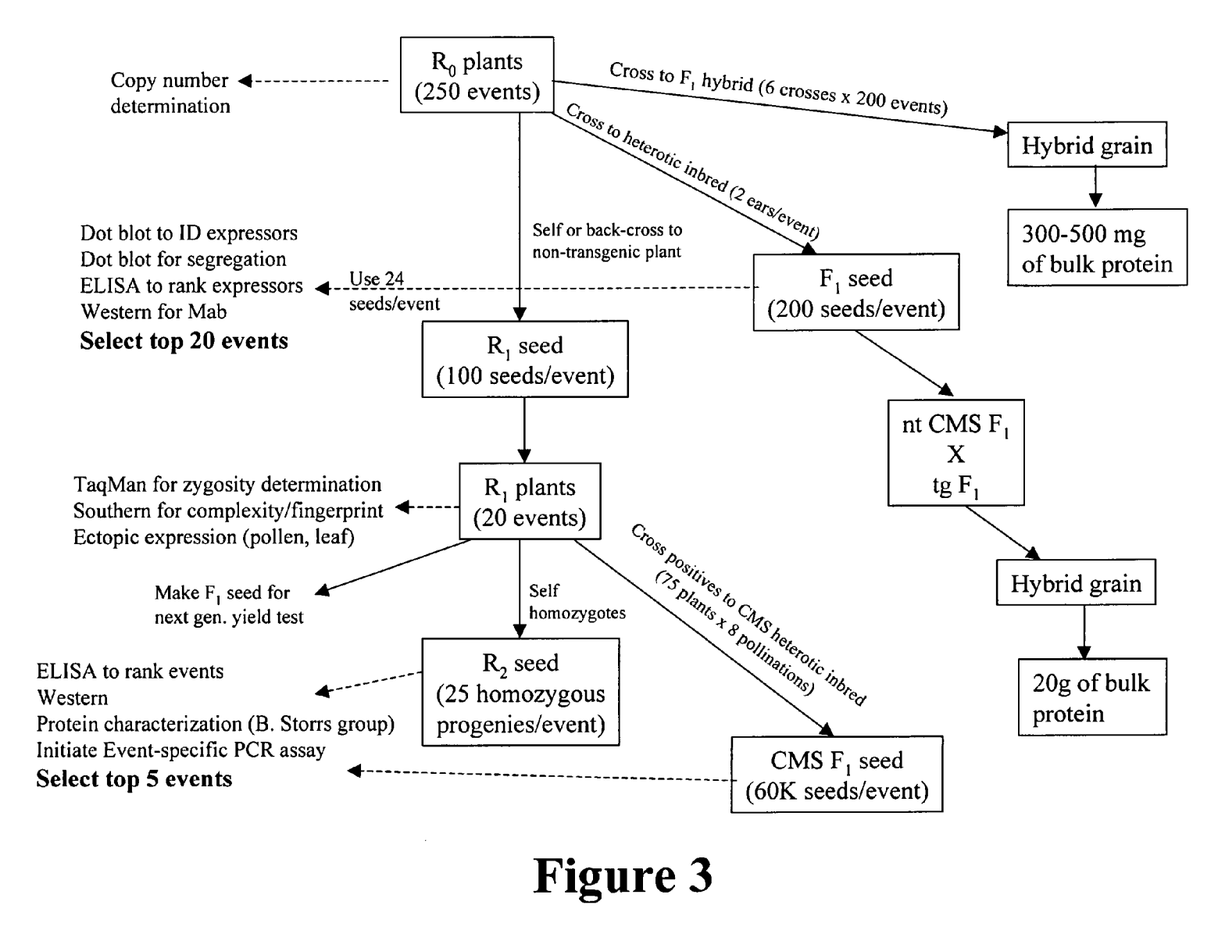
FIG. 3 sets forth an illustrative schematic of a $R_0$ and $R_1$ production and breeding approach.

In one aspect, fertile $R_2$ plants cross-pollinate a group or set of heterotic corn plants. In another aspect, which can be combined with cross-pollination of heterotic corn plants, the fertile $R_2$ plants are self-pollinated, backcrossed or both (see FIG. 3). An illustrative cross to a heterotic corn plant is set forth in Example 5. In a preferred aspect, the heterotic plant is an inbred and is cytoplasmic male sterile, which is not restored by such a cross. In another preferred aspect, the heterotic plant is an inbred that is either not cytoplasmic male sterile or any cytoplasmic male sterility is restored upon the cross, allowing for open pollination.

Figure 4:
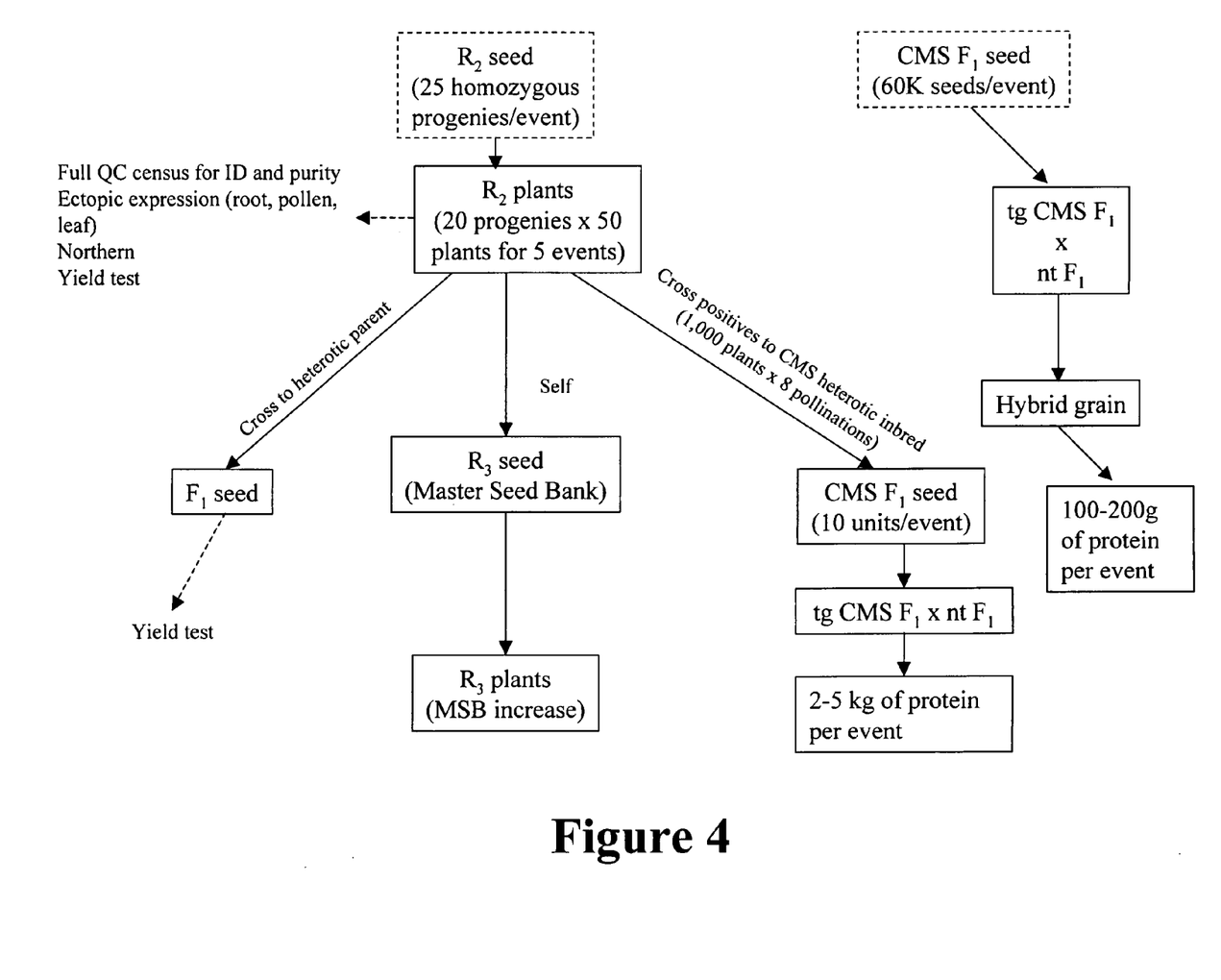
FIG. 4 sets forth an illustrative schematic of a $R_2/R_3$ production and breeding approach.

In a preferred aspect, a single set or group of fertile $R_2$ corn plants having a genome comprising a nucleic acid molecule encoding a pharmaceutically active protein can be used to cross-pollinate heterotic corn plants to form seed and to self-pollinate or be used to backcross to a non-transformed inbred parent. Such an approach is illustrated in FIG. 4.

Heterotic plants pollinated by $R_2$ corn plants can be planted and grown to produce $F_1$ hybrids ($-/R_2$). Pharmaceutically active proteins can be isolated from selfed $F_1$ corn hybrids. Alternatively or in combination with isolating pharmaceutically active proteins from the $F_1$ corn hybrids ($-/R_2$), the $F_1$ corn hybrids can be used to pollinate a recipient plant or be pollinated by a second plant or group of plants. While $F_1$ corn hybrids ($-/R_2$) comprising a nucleic acid molecule encoding a pharmaceutically active protein can be pollinated by any corn plant, it is preferred that the plant is non-transgenic. In a preferred aspect, an $F_1$ corn hybrid ($-/R_2$) is male sterile, preferably cytoplasmically male sterile.

It is preferred that the yield of pharmaceutically active protein is greater than 0.001 mg per gram of dry grain tissue in pollinated $F_1$ hybrids ($-/R_2$). In more preferred aspects, the yield of pharmaceutically active protein is greater than 0.01 mg, 0.05 mg, 0.1 mg, 0.3 mg, 0.5 mg, 0.7 mg or 0.9 mg per gram of dry grain tissue in such plants.

In a preferred aspect, each $R_2$ plant can be used to pollinate two or more heterotic ears or plants. In this aspect, it is preferred that each $R_2$ plant is used to generate more than 200, 400, 600, 800, 1,000, 1,200, 1,400 or 1,600 $F_1$ hybrid seeds ($-/R_2$). In a preferred protein production aspect, a set or group of transgenic $F_1$ hybrids ($-/R_2$) is of a sufficient size to provide greater than 200,000, 300,000, 400,000, 500,000, 600,000, 700,000, 800,000, 1,000,000, 1,500,000 or 2,000,000 seeds when pollinated with a second plant or group of plants.

In a protein production aspect where transgenic $F_1$ hybrids ($-/R_2$) are pollen recipient, self-pollinated or used to pollinate, sufficient recipient plants are preferred that can provide greater than 0.2 kg, 0.5 kg, 1 kg, 2 kg, 3 kg, 4 kg, or 6 kg of pharmaceutically active protein.

In an aspect of the present invention, a group or set of $R_3$, $R_4$ or subsequent generation corn plants can be used to pollinate one or more recipient corn plants for protein production, breeding, or both. Such a group or set of $R_3$, $R_4$ or subsequent generation plants can be the result of a single transformation experiment or the result of multiple transformation experiments. In one aspect, the group or set of $R_3$, $R_4$ or subsequent generation plants comprising a nucleic acid molecule encoding a pharmaceutically active protein used to cross-pollinate one or more recipient plants is greater than or equal to 2, 5, 10, 20, 25, 30, 40, 50, 60, 70, 80, 90, 100, 250, 500, 750, 1,000, 1,250, 1,500 or 2,000 $R_3$, $R_4$ or subsequent generation plants. Moreover, in this aspect the number of recipient plants is at least or equal to 2, 5, 10, 20, 25, 30, 40, 50, 60, 70, 80, 90, 100, 250, 500, 750, 1,000, 1,250, 1,500 or 2,000 recipient plants.

In one aspect, fertile $R_3$, $R_4$ or subsequent generation plants cross-pollinate a group or set of heterotic corn plants. In another aspect, which can be combined with cross-pollination of heterotic corn plants the fertile $R_3$, $R_4$ or subsequent generation plants are self-pollinated, backcrossed or both. In a preferred aspect, the heterotic plant is an inbred and is cytoplasmic male sterile, which is not restored by such a cross.

In a preferred aspect, a single set or group of fertile $R_3$, $R_4$ or subsequent generation corn plants having a genome comprising a nucleic acid molecule encoding a pharmaceutically active protein can be used to cross-pollinate heterotic corn plants to form seed and to self-pollinate or be used to backcross to a non-transformed inbred parent.

Heterotic plants pollinated by $R_3$, $R_4$ or subsequent generation corn plants can be planted and grown to produce $F_1$ hybrids. Pharmaceutically active proteins can be isolated from selfed $F_1$ corn hybrids. Alternatively or in combination with isolating pharmaceutically active proteins from the $F_1$ corn hybrids, the $F_1$ corn hybrids can be used to pollinate a recipient plant or be pollinated by a second plant or group of plants. While $F_1$ corn hybrids comprising a nucleic acid molecule encoding a pharmaceutically active protein can be pollinated by any corn plant, it is preferred that the plant is non-transgenic. In a preferred aspect, an $F_1$ corn hybrid is male sterile, preferably cytoplasmically male sterile.

It is preferred that the yield of pharmaceutically active protein is greater than 0.001 mg per gram of dry grain tissue in pollinated $F_1$ hybrids. In more preferred aspects, the yield of pharmaceutically active protein is greater than 0.01 mg, 0.05 mg, 0.1 mg, 0.3 mg, 0.5 mg, 0.7 mg or 0.9 mg per gram of dry grain tissue in such plants.

In a preferred aspect, each $R_3$, $R_4$ or subsequent generation plant can be used to pollinate two or more heterotic ears or plants. In this aspect, it is preferred that each $R_3$, $R_4$ or subsequent generation plant is used to generate more than 200, 400, 600, 800, 1,000, 1,200, 1,400 or 1,600 $F_1$ hybrid seeds. In a preferred protein production aspect, a set or group of transgenic $F_1$ hybrids is of a sufficient size to provide greater than 200,000, 300,000, 400,000, 500,000, 600,000, 700,000, 800,000, 1,000,000, 1,500,000 or 2,000,000 seeds when pollinated with a second plant or group of plants.

In a protein production aspect where transgenic $F_1$ hybrids are pollen recipient, self-pollinated or used to pollinate, sufficient recipient plants are preferred that can provide greater than 0.2 kg, 0.5 kg, 1 kg, 2 kg, 3 kg, 4 kg, or 6 kg of pharmaceutically active protein.

The present invention also provides a method for screening and selecting pharmaceutically active events in several generations including: obtaining a fertile $R_0$ plant and self-pollinating the $R_0$ plant to obtain $R_1$ seed, or cross-pollinating to an inbred plant of the same genetic background to produce $R_1$ seed or both. Positive events can be advanced to the next generation on the basis of high pharmaceutically active protein expression, genetic segregation pattern, copy number or protein quality or a combination of such qualities or traits (see, for example, without limitation, example 3). $R_1$ plants can be self-pollinated or cross-pollinated to an inbred of same genetic background to produce $R_2$ seed, or crossed to selected inbred lines for initiation of trait integration, usually in a heterotic background. Selection of appropriate events based on stability of pharmaceutically active protein expression, quality of protein, quantity of protein, genetic segregation pattern and zygosity and confirmation of copy number can occur during, for example, the advancement of homozygous $R_2$ progenies to the $R_3$ generation, self-pollination or open pollination of the $R_3$ plants or cross pollinating to an inbred of the same genetic background to produce $R_4$ seed. Selection of the most suitable event can be made based on factors such as the stability of pharmaceutically active protein expression over three generations, event purity, for example, as determined by Southern analysis or event specific PCR, and agronomic quality. Seed from selected progenies can be pooled to form a master seed bank or grown as $R_4$ plants and open-pollinating or crossing to an inbred of the same genetic background to make $R_5$ seed. Such processes can be repeated to maintain a master seed bank as needed.

Methods of the present invention allow for the selection of any number of plants to be taken into a subsequent generation for breeding purposes.

In one aspect of the present invention, about between 25 and 500, more preferably about between 100 and 400, or about between 200 and 300 $R_0$ events are selected for subsequent breeding.

In one aspect of the present invention, about between 2 and 50, more preferably about between 10 and 30, or about between 15 and 25 $R_1$ events are selected for subsequent breeding.

In one aspect of the present invention, about between 2 and 50, more preferably about between 10 and 30, or about between 15 and 25 $R_2$ events are selected for subsequent breeding.

In one aspect of the present invention, about between 1 and 20, more preferably about between 2 and 10, or about between 3 and 8 $R_3$ events are selected for subsequent breeding.

In one aspect of the present invention, about between 1 and 20, more preferably about between 2 and 10, or about between 3 and 8 $R_4$ events are selected for subsequent breeding.

In one aspect of the present invention, about between 1 and 20, more preferably about between 2 and 10, or about between 3 and 8 $R_5$ and subsequent generation events are selected for subsequent breeding.

In one aspect of the present invention, about between 5,000 and 100,000, more preferably about between 20,000 and 80,000, or about between 55,000 and 65,000 $R_0$ seeds are selected for subsequent breeding.

In such aspects, it is preferred that $R_0$ seeds are selected to be hemizygous for the pharmaceutically active protein trait. It is also preferred that $R_1$, $R_2$, $R_3$, $R_4$ and $R_5$ and subsequent generation seeds are selected to be homozygous for the pharmaceutically active protein.

The following examples are illustrative and not intended to be limiting in any way.

EXAMPLES

Example 1

A vector is engineered to allow for creation of transgenic plants that express an antibody in the corn seed. The vector pMON68466 is engineered by standard molecular biology methods (Ausabel et al., *Current protocols in molecular biology*, John Wiley and Sons (2003), WO 98/10062). It contains, in order, a cassette to express the antibody heavy chain, a cassette to express the antibody light chain, and a cassette to express the plant selectable marker, NPTII. Both the heavy chain and light chain cassettes contain, in order, the rice glutellin promoter, and portion of its 5' leader (WO 98/10062); the maize HSP70 intron, and a portion of the surrounding exon (U.S. Pat. No. 5,859,347); a tobacco extensin signal peptide, and a portion of the preceding 5' leader (U.S. Pat. No. 6,140,075); the mature antibody coding region; and the soy small subunit 3' end (Christou et al., Biotechnology, 9:957-962 (1991); WO 00/09721). The selectable marker cassette contains, in order, a CaMV 35S promoter, and a portion of its 5' leader, the coding region, and an *Agrobacterium* nopaline synthase 3' end (similar to U.S. Pat. No. 6,140,075). After construction and vector purification, the vector is linearized by cutting at the NotI restriction sites. The NotI restriction site is located between an antibody heavy chain cassette and after a NPTII cassette. The quality of this DNA fragment is confirmed by restriction mapping. Once confirmed, the purified DNA fragment is used to create transgenic maize plants using a methodology essentially as set forth in WO 98/10062.

Example 2

An $R_0$ greenhouse project is initiated using an antibody construct similar to that of Example 1. Plants hemizygous for an antibody trait similar to that of Example 1 are brought to the greenhouse (a total of 310 events). Plants from the greenhouse are self pollinated or backcrossed for generation advance, crossed to the inbred host to create materials for screening and generation advance (when the transgenic female pollination was unsuccessful), and crossed to hybrid plants to produce grain for a protein deliverable (300 mg). Seed set varies across different types of crosses. Selfed seed exhibit from 0 to 74 g of seed per ear, crosses to the inbred host exhibit from 0 to 100.6 g per ear, and crosses to hybrid ears were harvested in bulk but averaged ~75 mg per ear.

A total of 408 crosses are made to the inbred host line (more than total event numbers because in some instances there are multiple plants per event, or multiple pollinations if getting seed was thought to be difficult). Twenty-four seed samples of these ears are then taken and analyzed for protein and expression. Dot blots are performed to identify expressing events. The expressing events are then screened via ELISA to quantify expression in mg protein/gram of dry grain produced (11-15% moisture). A total of 1841 cross-pollinations are made to the hybrid female yielding ~130 kg of grain. The female hybrid used is LH198/LH192. The average estimated yield on this material is between 5-7 µg antibody per gram of seed.

Example 3

The seed screening strategy implemented at the $R_0$ stage of product development can include a sample of seeds from each productive ear that represents a unique transgenic event to be processed and tested for the presence and concentration of protein. For an antibody trait, this is done through single seed analysis by Western dot blot, followed by determining the recombinant protein concentration in the extract by ELISA. Typically, only $R_1$ seed is analyzed from each event, but in this instance, both testcross seed and $R_1$ seed are analyzed to determine which seed more closely predicts event performance in subsequent generations.

When available on the ear, 24 seed of each testcross ear and 8 seed of $R_1$ ears are obtained. In addition to the screening of $R_1$ seed, testcross seed is processed first through two rounds of seed screening by the Western dot blot technique. Individual dry seed weights (11-15% moisture) are made and seeds are crushed by the Sawz-all method (a motorized device). Each seed received 4 mL of seed extraction buffer (100 mM Tris Base, 20 mM NaCl) and the sample is subsequently extracted at room temperature for 1 hour while shaking. The samples are gravity settled for 20 minutes and aliquoted into a 96-well dilution plate. The dilution plate also contained a reference standard spiked into null corn seed extract at levels nominally representing 0, 0.04, 0.2 and 1.0 mg/gram seed. An equal volume of PBS was added to the dilution plate, the samples are mixed and applied onto a nitrocellulose membrane using a 96-pronged replica-plating tool. The blot is detected for antibody using an HRP-conjugated goat anti-human, HC specific detection antibody. Spots are visualized using the ECL™ chemiluminescent detection kit (Amersham, Piscataway, N.J.). Images are captured by an electronic imager (Fuji LAS 1000, Stanford, Conn.) and evaluated for antibody expression levels relative to the standard spiked into corn seed extract. The entire blotting experiment is replicated, and any significant differences are noted. Extracts from events with positive expression of protein in the seed are advanced to a quantitative ELISA test (Mushens et al., *J. Immunol. Methods*, 162(1):77-83 (1993); Vilaseca et al., *Hybridoma*, 16(6):557-562 (1997); Butler et al., *Mol. Immunol.*, 23(9):971-982 (1986)). Eight $R_1$ seed from expressing events or events that had no $F_1$ seed are tested for protein expression using the same dot blot technique. Any event not having $F_1$ seed for the first set of dot blot screens is screened by $R_1$ seed.

Out of the 220 events recovered in the testcross seed about 46% of the events expressed antibody in the seed. The data for the selfed seed includes seed from events known to express antibody as shown by their $F_1$ crosses and events that had no testcross seed available for testing. Only 55 events yielded both self and testcross seed that could be analyzed by the dot blot method. Of the events generated by transformation, a total of 257 unique transgenic events were recovered. All extracts expressing protein are retained for ELISA testing.

The productivity of a transgenic event can be ranked against other events by determining the recombinant protein content in the seed extracts obtained from the dot blot analysis. To do this, ELISAs are performed on positive extracts used in the dot blots assay. The testcross seed and the selfed seed are assayed by ELISA to compare overall performance of each event and to determine which seed system is most representative of event performance. Selfed seed represents a matrix of gene dosages and expressing seed may be either homozygous or hemizygous for the trait. This gene dosage affects protein production in a positive way but can complicate the analysis of events, as endosperm zygosity is not known for the seeds tested at this stage. Testcross seed possess a single copy of the transgenic event (unless the DNA is integrated into multiple loci within the genome). Also, testcross seed set is often healthier than seed set on the regenerated plant. By assaying the testcross seed, single gene dosage can more closely represent the productivity of the event in this and future generations.

Up to four seed extracts are obtained from frozen extracts of seed that expressed protein according to the dot blot procedure. These are assayed for antibody content by a sandwich ELISA. The assay uses an antibody fragment, F(ab)2, to capture the recombinant protein by the constant region of the heavy chain and an anti-human kappa chain antibody that is conjugated to horseradish peroxidase as the secondary, detection antibody. A reference standard is used to make a standard curve and non-transgenic seed extracts were used as negative controls. ELISA values from each of the four seed extracts are averaged and the resulting number represented the transgenic event.

Figure 5:
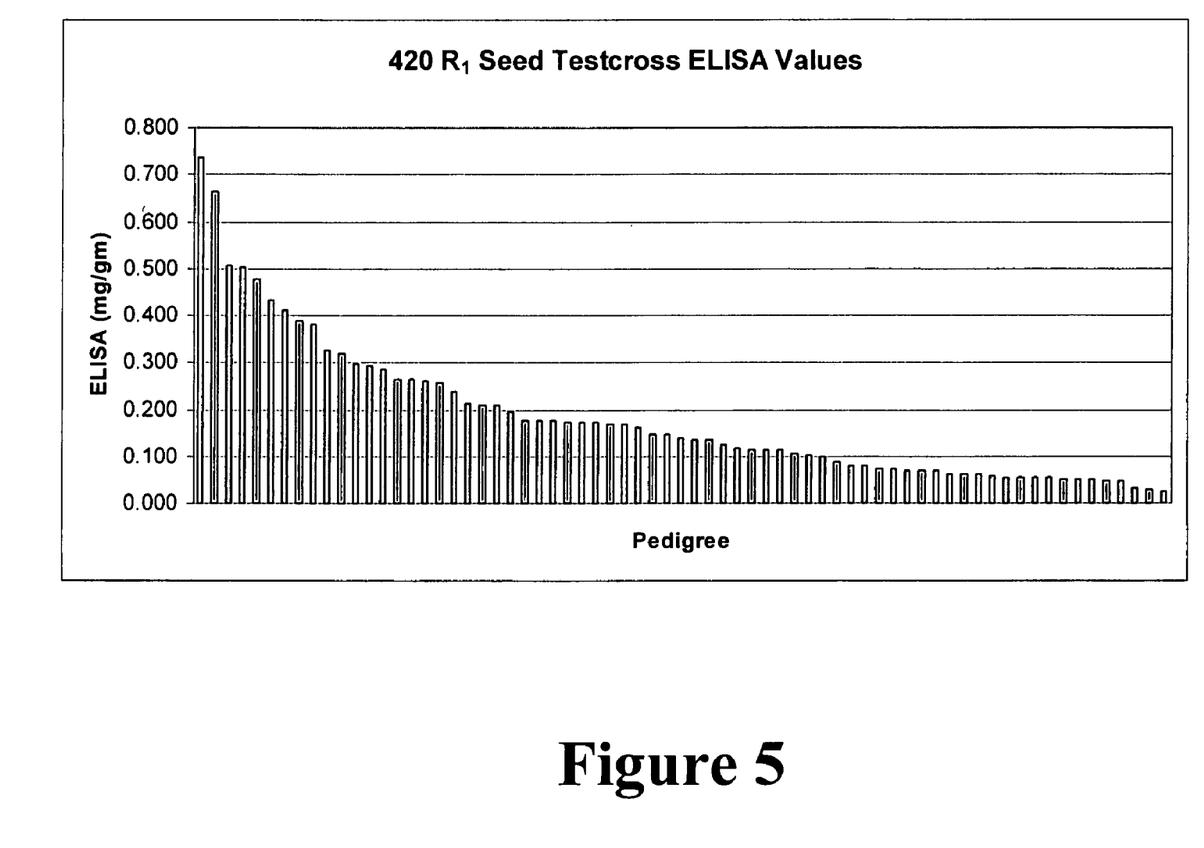
FIG. 5 sets forth a bar graph representing the population of ELISA values obtained on 69 events analyzed in $R_1$ test cross seed.
Figure 6:
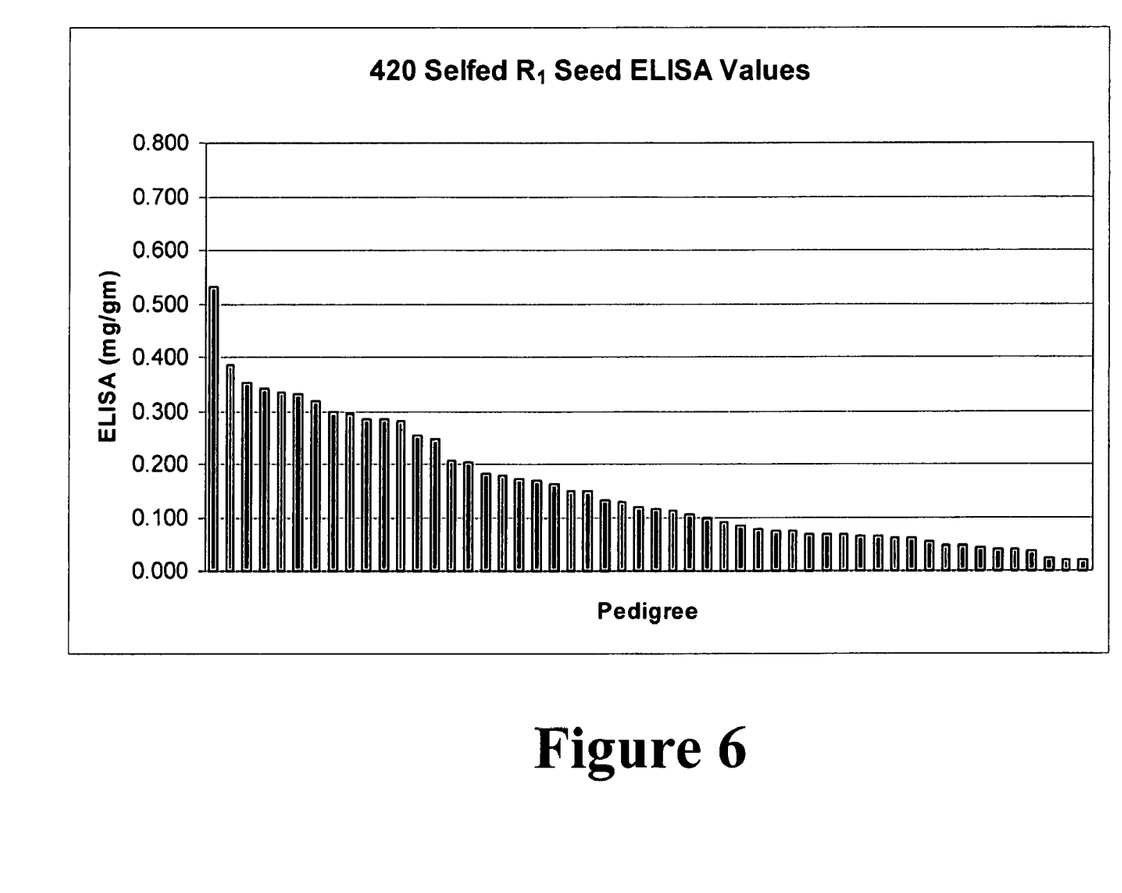
FIG. 6 sets forth a bar graph representing the population of ELISA values obtained from 52 selfed events in $R_1$ seed generation.

ELISA results for an antibody project can be found in FIGS. 5 and 6. 101 testcross events expressed protein, ELISA did not detect protein in 22 events (below detection limits) and extracts on 10 events are used up due to repeated ELISA failures. In total, 69 testcross events and 52 selfed events gave reliable ELISA results. Reciprocal crosses are eliminated from this analysis (10 events). FIG. 5 and Table 1 are graphs of the antibody expression for each event analyzed. Table 1 gives the range of the ELISA values for each of these seed populations.

TABLE 1

Range of ELISA values for the two seed types

|  | No. assayed | Low (mg/gm) | High (mg/gm) |
|---|---|---|---|
| Selfed | 52 | 0.31 | 0.531 |
| Testcrossed | 101 | 0.026 | 0.736 |

Figure 7:
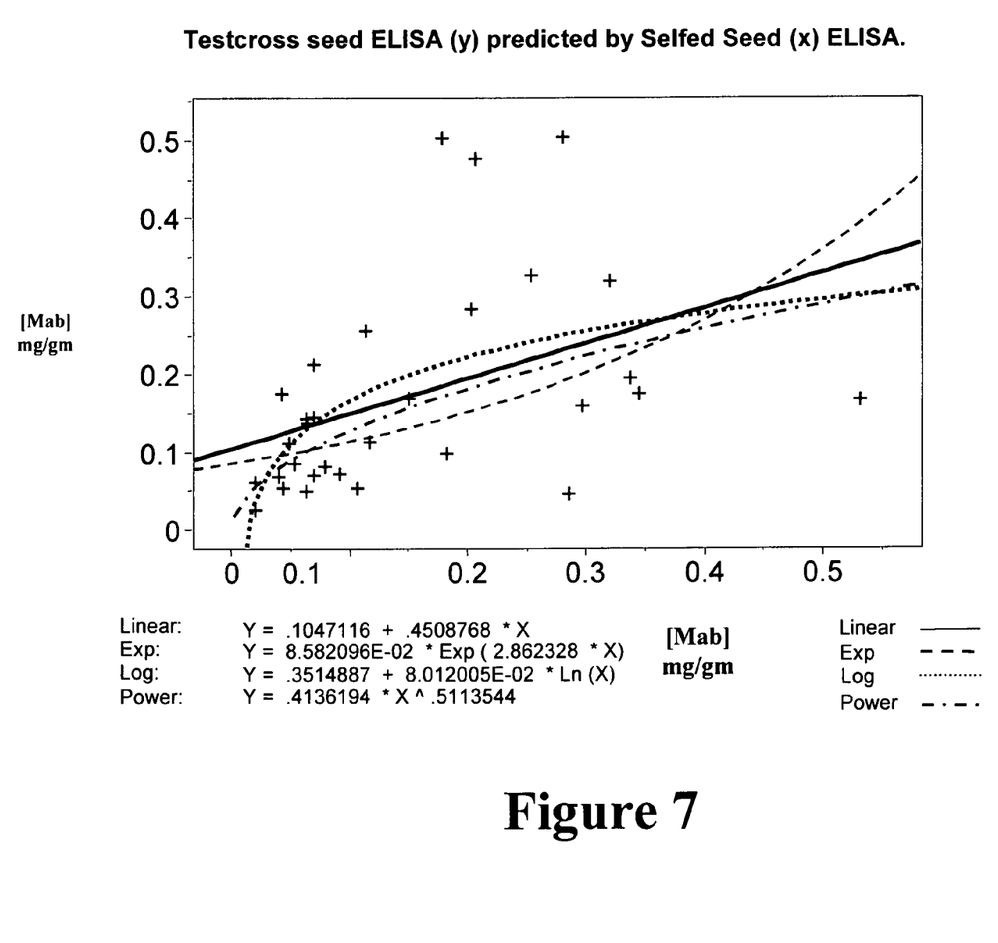
FIG. 7 sets forth a plot of regression models of $R_1$ seed ELISA values.

Regression analysis on the few events (31 of 55 possible) that had both $R_1$ and $F_1$ ELISA data available is performed. Of the four models developed to define the relationship between the data, linear, log, exponential and power, the strongest correlation between the two data sets was found in a power function (Correlation coefficient=0.59). Residuals are large for all functions and R-squared values were less than 0.35. ELISA values obtained on selfed seed are average values from genetically heterogeneous seed. On average the selfed seed yield a gene dosage of 2 while in testcross seed this number is known to be 1. The genetics of the selfed seed can skew the data thereby reducing the strength of the regression models applied to the data. However, higher expression from events in selfed seed also gives higher expression in testcross seed. Furthermore, factors other than just gene dosage affect the performance of gene expression within any given event (see FIG. 7).

Example 4

A field is planted with populations of $R_1$ plants that were segregating for expression of an antibody similar to that of Example 1. Plants from this field are used to identify the homozygous plants expressing the antibody, and then selfed to increase the seed available for generation advance. The fields are also used to produce transgenic $F_1$ hybrid seed expressing the antibody of Example 1 which can be used the following generation for production of large quantities of hybrid grain for extraction of the purified protein. The field is also used to produce part of the $F_1$ hybrid seed produced for purified protein extraction purpose. An alternative process currently uses $F_1$ hybrid seed that is produced in the previous $R_0$ generation to cross to large numbers of cms hybrid female plants to produce even larger quantities of transgenic grain for purification of up to 20 grams of purified protein.

The field contains five $R_1$ events of an antibody similar to that of Example 1, containing from 10 to 130 seeds each. An additional four $F_1$ events of an antibody similar to that of Example 1, containing from 26 to 86 seeds each are also planted. These events are not selfed in the $R_0$ generation, and are crossed to A634 non-transgenic inbred to recover some seed of these events for generation advancement. The rows of transgenic plants are surrounded by rows of non-transgenic plants of the sterile inbred corn line 90DJD28CMS.

The $R_1$ plants and the $F_1$ plants are screened for expression of the pharmaceutically active protein. Plants that tested positive for the expression of the pharmaceutically active protein are selfed to produce $R_2$ seed. Additionally, pollen from the plants that tested positive for the pharmaceutically active protein are used to pollinate non-transgenic corn plants 90DJD28CMS to produce $F_1$ hybrid seed that expresses an antibody similar to that of Example 1. Portions of the $F_1$ hybrid seed is processed to extract the pharmaceutically active proteins and the remainder was retained for future planting in a subsequent generation to produce additional antibodies similar to that of Example 1. The following table lists the number of plants, the number of plants tested positive for the pharmaceutically active protein, and the number of crosses made for each of the nine events.

| Event | Type of Seed | No. of Plants | No. of Positive Plants | No. of Selfs |
|---|---|---|---|---|
| ZM__A4227 | $R_1$ | 115 | 90 | 90 |
| ZM__A4019 | $R_1$ | 130 | 100 | 100 |
| ZM__A3680 | $R_1$ | 91 | 66 | 66 |
| ZM__A4241 | $R_1$ | 7 | 7 | 7 |
| ZM__A3760 | $R_1$ | 121 | 84 | 84 |
| A634/ZM__A3782 | $F_1$ | 26 | 22 | 22 |
| A634/ZM__A4223 | $F_1$ | 77 | 20 | 20 |
| A634/ZM__A3716 | $F_1$ | 37 | 13 | 13 |
| A634/ZM__A3798 | $F_1$ | 86 | 86 | 86 |

Example 5

$R_2$ plants are planted. Homozygous $R_1$ plants from selected events are seeded at a minimum population of 50 plants per homozygous derived progeny, with up to 25 homozygous derived progenies per event. These homozygous derived plants are screened for phenotype and, as a result, plants and or progenies that do not fit the expected phenotype, are eliminated prior to pollination. Selected progenies or plants are self-pollinated to produce $R_3$ seed. Additionally, pollen from selected progenies or plants are used to generate $F_1$ seed by pollinating recipient female heterotic plants. Up to 10 pollinations from each $R_2$ plant are made to the intended female recipient. This $F_1$ seed is used in the next generation to produce an antibody similar to that of Example 1. Additionally, pollen from selected progenies or plants are used to make $F_1$ seed for yield test purposes in the next generation. These crosses are made to different inbred lines such as 5750, 35CXZ3, 01INL1 and 90DJD28.

Example 6

A field is planted with $R_3$ inbred corn plants that are homozygous for expression of the pharmaceutically active protein of Example 1. $R_3$ plants from this field are used to verify the homozygous plants expressing the protein of Example 1. $R_3$ plants are also selfed to increase the seed available for generation advance; and used to produce transgenic $F_1$ hybrid seed expressing the antibody of Example 1, which can be used the following generation for production of large quantities of hybrid grain for extraction of the purified protein. $R_3$ plants are further used to pollinate the sterile $F_1$ hybrid seed that was produced in the previous $R_2$ generations and to cross to large numbers of non-transgenic hybrid male pollinator plants to produce even further quantities of transgenic grain for purification of up to 150 grams of purified antibody of Example 1.

Four $R_3$ events of the antibody of Example 1, containing approximately 1,000 seeds each are planted in a field nursery. Each range of transgenic plants is bordered by a range of non-transgenic sterile inbred corn plants 90DJD28CMS, that is used for making the crosses to produce $F_1$ seed.

The $R_3$ plants are screened to verify that they expressed the pharmaceutically active protein. All confirmed positive plants are self-pollinated to produce $R_4$ seed. Additionally, pollen from the plants that tested positive for the antibody of Example 1 are used to pollinate sterile 90DJD28CMS corn plants to produce $F_1$ hybrid seed that expresses the pharmaceutically active protein. This seed is retained for future planting in a subsequent generation to produce additional pharmaceutically active protein.

The following table lists the number of plants confirmed positive for the pharmaceutically active protein, and the number of crosses made for each of the four events.

| Event | Type of Seed | No. of Crosses |
| --- | --- | --- |
| ZM__A3006 | $R_3$ | 2033 |
| ZM__A2963 | $R_3$ | 2699 |
| ZM__A2962 | $R_3$ | 2405 |
| ZM__A2636 | $R_3$ | 990 |

Another field is planted where $F_1$ sterile hybrid versions of two events of plants containing an antibody of Example 1 are grown in alternative rows with $F_1$ fertile hybrid plants of a similar genetic background that did not contain the protein. The seed for the transgenic female plants is produced the season before in a field by crossing transgenic inbred plants expressing the pharmaceutically active protein to a non-transgenic sterile inbred corn plant 90DJD28CMS. This produced the male sterile transgenic $F_1$ plants used as the female parent in the field. Each field contained a series of bays containing 4 rows of transgenic $F_1$ sterile female plants alternating with two rows of non-transgenic male pollinator plants of the genotype 90DJD28xA634. Total transgenic area is 2.8 acres for each of the two events. The sterile plants containing the pharmaceutically active protein are pollinated by the fertile plants, producing $F_1$ grain containing the pharmaceutically active protein. The harvested $F_1$ grain is processed to extract the antibody of Example 1.

Example 7

A field is planted with $R_4$ inbred corn plants that is homozygous for expression of the antibody of Example 1. Plants from this field are used to verify the homozygous plants expressing the antibody of Example 1. Such plants are selfed to increase the seed available for generation advance; and used to produce transgenic $F_1$ hybrid seed expressing the antibody of Example 1, which is used in the following generation for production of large quantities of hybrid grain for extraction of the purified protein. They are also used to pollinate sterile $F_1$ hybrid seed that is produced in the previous $R_3$ generations and for crosses to large numbers of non-transgenic hybrid male pollinator plants in order to produce larger amounts of transgenic grain for purification of up to 1500 grams of purified protein.

One $R_4$ event of the antibody of Example 1, containing approximately 1,000 seeds each are planted in a field nursery. Each range of transgenic plants is bordered by a range of non-transgenic sterile inbred corn plants 90DJD28CMS, that is used for making the crosses to produce $F_1$ seed.

The $R_4$ plants are screened to verify that they expressed the antibody of Example 1. All confirmed positive plants are self-pollinated to produce $R_5$ seed. Additionally, pollen from the plants that tested positive for the pharmaceutically active protein is used to pollinate sterile 90DJD28CMS corn plants to produce $F_1$ hybrid seed that expresses the pharmaceutically active protein. This seed is retained for future planting in a subsequent generation to produce additional pharmaceutically active protein.

Another field is planted where $F_1$ sterile hybrid versions of one or two events of plants containing an antibody of Example 1 are grown in alternative rows with $F_1$ fertile hybrid plants of a similar genetic background that did not contain the protein. The seed for the transgenic female plants is produced the season before in a field by crossing transgenic inbred plants expressing the pharmaceutically active protein to a non-transgenic sterile inbred corn plant 90DJD28CMS. This produced a male sterile, transgenic $F_1$ plant. Each field contained a series of bays containing 4 rows of transgenic $F_1$ sterile female plants alternating with two rows of non-transgenic male pollinator plants of the genotype 90DJD28xA634. Total transgenic area is approximately 10 acres for each event. The sterile plants containing the pharmaceutically active protein are pollinated by the fertile plants, producing $F_1$ grain containing the pharmaceutically active protein. The harvested $F_1$ grain is processed to extract the pharmaceutically active protein.

All publications and patent applications mentioned in this specification are herein incorporated by reference to the same extent as if each individual publication or patent application was specifically and individually indicated to be incorporated by reference.

What is claimed is:

1. A method of producing a pharmaceutically active protein in corn plants comprising:
    a) obtaining a fertile $R_0$ corn plant comprising a nucleic acid molecule encoding said pharmaceutically active protein;
    b) cross-pollinating a first set of hybrid corn plants with pollen produced by said $R_0$ corn plant;
    c) harvesting grain on said hybrid corn plant and harvesting seed from the first set of heterotic corn plants;
    d) isolating said pharmaceutically active protein from said grain on said first set of hybrid plants;
    e) planting and growing said seed from said heterotic corn plants to form $F_1$ hybrid plants; and
    f) isolating said pharmaceutically active protein from grain of $F_1$ hybrid plants.

2. The method according to claim 1, further comprising (g) cross-pollinating male sterile recipient $F_1$ hybrid plants with said $F_1$ hybrid plants.

3. The method according to claim 2, further comprising (h) isolating said pharmaceutically active protein from at least grain of said male sterile recipient plants.

4. The method according to claim 1, further comprising cross-pollination of a corn plant that has a similar genetic background but lacks a nucleic acid molecule encoding said pharmaceutically active protein with pollen produced by said $R_0$ corn plant.

5. The method according to claim 1, further comprising self-pollination of said fertile $R_0$ corn plant.

6. The method according to claim 5, further comprising planting and growing seeds of said selfed-$R_0$ corn plant to form $R_1$ plants.

7. The method according to claim 6, further comprising screening seeds of said $R_1$ plants for expression of said pharmaceutically active protein.

8. The method according to claim 6, further comprising self-pollination of said $R_1$ plants that are homozygous for an allele of said nucleic acid molecule encoding said pharmaceutically active protein.

9. The method according to claim 6, further comprising cross-pollinating a second set of heterotic corn plants with pollen produced by said $R_1$ plants, wherein said $R_1$ plants are homozygous or heterozygous or mixtures thereof for an allele of said nucleic acid molecule encoding said pharmaceutically active protein.

10. The method according to claim 1, wherein said cross-pollinating a first set of hybrid corn plants further comprises cross-pollinating a first set of heterotic corn plants with pollen produced by said $R_0$ corn plant.

11. A method of producing a pharmaceutically active protein in corn plants comprising:

a) obtaining a fertile $R_0$ corn plant comprising a nucleic acid molecule encoding said pharmaceutically active protein;

b) cross-pollinating a first set of hybrid corn plants with pollen produced by said $R_0$ corn plant; and c) harvesting grain on said hybrid corn plant and harvesting seed from the first set of heterotic corn plants.

12. The method according to claim 1, further comprising d) isolating said pharmaceutically active protein from said grain on said first set of hybrid plants.

13. The method according to claim 1, further comprising e) planting and growing said seed from said heterotic corn plants to form $F_1$ hybrid plants.

* * * * *